United States Patent [19]

Davies et al.

[11] 4,269,820

[45] May 26, 1981

[54] SAFEGUARDED TOXIC CHEMICAL COMPOSITIONS CONTAINING EFFECTIVE EMESIS-INDUCING S-TRIAZOLO-[1,5-α]PYRIMIDINE DERIVATIVES

[75] Inventors: George E. Davies, Wilmslow; David M. Foulkes, Henly-on-Thames, both of England

[73] Assignee: Imperial Chemical Industries Limited, London, England

[21] Appl. No.: 104,758

[22] Filed: Dec. 18, 1979

Related U.S. Application Data

[63] Continuation of Ser. No. 873,497, Jan. 30, 1978, abandoned, which is a continuation-in-part of Ser. No. 830,765, Sep. 6, 1977, Pat. No. 4,160,017, which is a continuation of Ser. No. 716,801, Aug. 23, 1976, Pat. No. 4,046,552.

[30] Foreign Application Priority Data

Feb. 11, 1977 [GB] United Kingdom ............... 5708/77
Apr. 29, 1977 [GB] United Kingdom ............. 18008/77

[51] Int. Cl.$^3$ .................. A61K 7/047; A61K 7/08; A61K 7/15; A61K 7/46
[52] U.S. Cl. ................................. 424/10; 43/124; 43/131; 71/67; 71/70; 71/117; 252/71; 252/187 H; 252/364; 252/365; 252/366; 252/DIG. 5; 252/DIG. 8; 252/522 R; 424/2; 424/17; 424/47; 424/71; 424/73; 424/84; 424/149; 424/213; 424/219; 424/232; 424/251; 424/254; 424/300; 424/306; 424/333; 424/346
[58] Field of Search .................. 424/10, 219, 2, 17, 424/47, 71, 73, 84, 149, 213, 232, 251, 254, 300, 306, 333, 346; 252/365, 366, 71, 187 H, 364, 15, 22, DIG. 5, DIG. 8; 71/91, 67, 70, 117; 43/124, 131

[56] References Cited

U.S. PATENT DOCUMENTS

| | | | |
|---|---|---|---|
| 1,507,029 | 9/1924 | Prittie | 424/10 |
| 2,258,414 | 10/1941 | Kvalnes | 424/10 |
| 2,265,196 | 12/1941 | Riley | 252/366 |
| 2,957,804 | 10/1960 | Shuyler | 424/10 |
| 3,080,327 | 3/1963 | Hay | 252/366 |
| 3,689,488 | 9/1972 | Dukes | 424/25 |
| 3,935,137 | 1/1976 | Minkoff | 260/17 R |
| 4,005,038 | 1/1977 | Minkoff | 260/17 R |
| 4,046,552 | 9/1977 | Davies et al. | 71/91 |
| 4,160,017 | 7/1979 | Davies et al. | 424/10 |
| 4,175,119 | 11/1979 | Porter | 424/10 |

FOREIGN PATENT DOCUMENTS

| | | |
|---|---|---|
| 2067846 | 8/1971 | France . |
| 348003 | 9/1960 | Switzerland . |
| 1234635 | 6/1971 | United Kingdom . |
| 1428361 | 3/1976 | United Kingdom . |
| 1486137 | 9/1977 | United Kingdom . |
| 15584176 | 9/1978 | United Kingdom . |
| 1507407 | 12/1978 | United Kingdom . |

OTHER PUBLICATIONS

H. Mattnew Treatment of Common Acute Poisonings, Churchill Livingstone, Edinburgh, London, 1972, 21-22.
Franklin Built-In Life Guard Time, Aug. 2, 1948, p. 32.
AMA Drug Evaluations, 2nd Ed., (1973), 817-818 Emetics, Apomorphine HCl Tartar Emetic Ipecac Syrup Cupric Sulfate.
Kefauver Wash. DC Sunday Star This Week, Mar. 20, 1949, Lets Stop Sleeping Pill Suicide.
Miskin, Virginia Medical-Monthly: 119-122, 1950, A Method for Prevention of Suicidal Deaths Caused by Barbituric acid.
Anon, J. A. M. A., 146(10), 977-7 Jul. 1951, Sleeping Pills Containing an Emetic Aid.
Davies et al., Nature New Biology, vol. 234, pp. 50-51, (1971).

*Primary Examiner*—Shep K. Rose
*Attorney, Agent, or Firm*—Cushman, Darby & Cushman

[57] ABSTRACT

An emetic composition comprising a toxic chemical substance which is other than a herbicidal bipyridylium quaternary salt, which is not intended for oral ingestion but when so orally ingested passes into the blood through the stomach and digestive tract and for which treatment by induction of emesis is medically advisable and an emetically effective amount of an emetically active s-triazolo-[1,5-α]pyrimidine derivative, the ratio of emetic to toxic chemical being such as to induce emesis when the composition is orally ingested.

8 Claims, No Drawings

SAFEGUARDED TOXIC CHEMICAL COMPOSITIONS CONTAINING EFFECTIVE EMESIS-INDUCING S-TRIAZOLO-[1,5-α]PYRIMIDINE DERIVATIVES

This is a continutation, of application Ser. No. 873,497, filed Jan. 30, 1978 now abandoned, which is a continuation-in-part of Ser. No. 830,765, filed Sept. 6, 1977, now U.S. Pat. No. 4,160,017, which is a continuation of Ser. No. 716,801, filed Aug. 23, 1976, now U.S. Pat. No. 4,046,552.

This invention relates to safeguarded chemical compositions, and in particular to safeguarded pesticidal chemical compositions.

There is, at the present time, in industrial, agricultural and domestic environments, a wide exposure of consumers throughout the world to chemical substances that are potentially toxic to human beings. Some of these substances are of necessity toxic to certain forms of life, for example pesticides and disinfectants. Pesticides, when used with due care, and in accordance with governmentally approved codes of practice and the manufacturers' or suppliers' instructions, present no hazard to human life. However, in spite of efforts to encourage safe handling practices, instances of misuse do occur resulting in the deaths of human beings. These include cases where liquid pesticides are swallowed, often by being mistaken for beverages.

Equally tragic, and more numerous, are deaths resulting from suicides caused by the deliberate ingestion of pesticides, in particular insecticides, or of chemical household products and drugs.

The present invention provides a means whereby toxic chemicals are made safer by including in them small quantities of an emetic substance. Then, if the toxic product is swallowed in dangerous quantities, emesis is likely to occur; this can result, in some cases, in rapid removal of the chemical composition from the stomach before lethal amounts of the chemical have been assimilated by the body.

There are a number of reasons why presently known substances having emetic properties are not generally suitable for widespread use in admixture with toxic chemicals as a means for reducing the risk of poisoning. Known emetics may be unsuitable for administration to human beings for a number of reasons; they may not be suitable for oral administration and may have to be given by another route, e.g. intravenous injection; they may be physically or chemically unstable over reasonable periods of time, alone or when in admixture with the toxic chemical; they may be per se environmentally unacceptable; they may have unsuitable toxicological properties; they may have highly undesirable side-effects; or they may be completely isoluble. In this respect the unfavourable properties of several known emetics are referred to in "Treatment of Common Acute Poisonings", edited by H. Matthew and A. A. H. Lawson, published by Churchill Livingstone, Edinburgh and London, 1972, at pages 21–22. Emetic drugs such as apomorphine are dangerous as they may induce protracted vomiting and shock. Apomorphine is unstable in air, oxidising readily, so that it is supplied as ampules for injection. Syrup of ipecacuanha has an emetic effect which is too slow and too uncertain, even at nearly lethal dosage rates. Furthermore the emetine content of the ipecacuanha may be absorbed and itself produce toxic effects.

Copper and antimony containing perparations, being metal salts and not biodegradable, could constitute an unacceptable environmental problem if the metal salts, in admixture with a pesticide, were to be regularly sprayed in the environment; in any event antimony is a highly poisonous substance in its own right. Matricaria comprises the ground-up heads of camomile plants and is unsuitable by being insufficiently soluble.

Rodenticide formulations have been proposed, for example as in Swiss Pat. No. 348003 and French Patent Application No. 2067846, which include such known emetic substances.

The s-triazolopyrimidine compounds deployed in the safeguarded toxic compositions, and method, of the present invention, are themselves described and claimed in our U.K. Pat. No. 1,234,635 and also in our U.S. Pat. No. 3,689,488. Methods for preparing the compounds are recited therein. The description of the latter patents is incorporated herein by reference. The foregoing patent specifications describe the anti-bronchospasmodic, anti-allergic and other pharmacologically useful properties of the compounds, but do not disclose their emetic properties.

In our copending application U.K. Application No. 15584/76 filed on April 15, 1976 (which does not form part of the published prior art) there are described and claimed compositions comprising a herbicidal bipyridylium quaternary salt and a triazolo [1,5-α] pyrimidine derivative, which compositions, if swallowed, tend to induce emesis, and thereby, expulsion of the composition. A corresponding patent application in the United States of America has given rise to U.S. Pat. No. 4,046,552.

At the time when the above-mentioned U.K. Patent Application No. 15584/76 was filed it was believed that the novel and particular compositions disclosed and claimed therein were a single, unusual, instance of compatibility and effectiveness; and that it was in no way obvious to extend the invention of the combination of emetic substance and herbicidal bipyridylium quaternary ion (e.g. paraquat) or salt so as to safen other toxic chemicals from oral ingestion, because the foregoing herbicides, when ingested are only slowly absorbed into the bloodstream by humans. Thus it was believed that there would be, in addition to a lack of speed of action against fast-acting poisons, some chemical and/or biological interference, or other incompatibility, between at least some toxic chemicals and the emetics.

It has now been found, suprisingly, that even fast-acting highly toxic substances, such as the intensely poisonous organo-phosphorus pesticides parathion (having an $LD_{50}$ of only 3 to 13 mg/kg in the rat) and malathion, can be substantially safened against poisoning by oral ingestion by admixing them with the emetic substances. This most remarkable discovery is supplemented by the further finding that the emetic substances can be readily formulated with a wide variety of toxic chemical substances without problems of incompatibility. Thus there appear to be few formulation or storage problems, and few instances of even a small degree of interference with the biological effects and mode of action of the emetic substances.

The wholly unique nature of the present invention is supported by the further unexpected finding that the emetic substances, in addition to being capable of inducing emesis, possess safening action by delaying uptake by the blood of a toxic chemical from the stomach and digestive tract (and do so even if emesis does not take place), by reducing the rate of gastric emptying. Gastric emptying generally means the passage from the stomach into the small intestine where digested food, and most ingested foreign compounds, e.g. drugs and pesticides, are absorbed into the body system. Thus the results of experiments with rats and mice (nonvomiting species) and monkeys (vomiting species) has shown gastric emptying to be significantly delayed at sub-emetic dosages. The speed, and dual mode, of action of the emetic substances with respect to mammals in this regard is a novel and surprising discovery.

According to the present invention there is provided an emetic chemical composition comprising a toxic chemical substance (other than a herbicidal bipyridylium quaternary salt) and an emetic which is an s-triazolo [1,5-α] pyrimidine derivative of the formula:

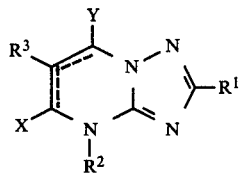

Formula I wherein $R^1$ is an amino, alkylamino, phenylalkylamino, dialkylamino, ureido, carboxyl, hydroxyalkyl or carbazoyl group; $R^2$ is an alkyl, cycloalkyl or alkenyl group; $R^3$ is hydrogen, halogen or an alkyl or hydroxyalkyl group; one of X and Y stands for an oxo or thioxo radical, and the other of X and Y stands for hydrogen or an alkyl radical, and when X stands for an oxo or thioxo radical, the nucleus contains a double bond between the carbon atoms in positions 6 and 7, and when Y stands for an oxo or thioxo radical, the nucleus contains a double bond between the carbon atoms in positions 5 and 6; and the base addition salts of a triazolo-pyrimidine derivative defined above which contains an acidic group; or an acylated derivative, or base addition salt thereof; the ratio of emetic to toxic chemical in the composition being such that a toxic dose of the composition tends to induce emesis. Preferably alkyl and alkenyl groups in the above definition contain not more than 6 carbon atoms. The s-triazolo [1,5-α] pyrimidine ring structure is numbered as shown below:

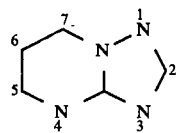

A preferred group of triazolo-pyrimidine derivatives for use in the compositions of the invention are those of the following formula (II):

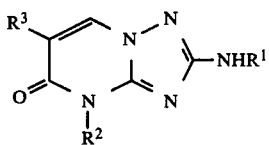

Formula II wherein $R^1$ is hydrogen or an alkyl radical containing from 1 to 4 carbon atoms, or an acyl radical of the formula $R^4.CO$—wherein $R^4$ is an alkyl or alkoxy radical containing from 1 to 4 carbon atoms or a chlorophenyl radical, $R^2$ is an alkyl or alkenyl radical containing from 1 to 4 carbon atoms, or a cyclopentyl radical, and $R^3$ is an alkyl radical containing from 1 to 4 carbon atoms.

Particular derivatives of 5-oxo-4,5-dihydro-s-triazolo [1,5-α] pyrimidine of use in the practice of the invention are:
2-amino-6-methyl-4-n-propyl-
2-acetamido-6-methyl-4-n-propyl-
6-methyl-4-n-propyl-2-n-propylamino-
2-amino-6-methyl-4-n-butyl-
2-amino-6-methyl-4-allyl-
2-amino-7-methyl-4-n-propyl-
2-dimethylamino-6-methyl-4-n-propyl-
2-di-n-propylamino-6-methyl-4-n-propyl-
2-isopropylamino-6-methyl-4-n-propyl-
2-p-chlorobenzamido-6-methyl-4-n-propyl-
2-ethoxythiocarbonylamino-6-methyl-4-n-propyl-
2-ethoxycarbonylamino-6-methyl-4-n-propyl-
2-(3-phenylureido)-6-methyl-4-n-propyl-
2-amino-4,6-di-n-propyl-
2-N,N-diacetylamino-6-methyl-4-n-propyl-
2-N-ethoxycarbonyl-N-α-phenylethylamino-6-methyl-4n-propyl-
2-amino-6-methyl-4s-butyl-
2-amino-6-methyl-4-cyclopentyl-
2-amino-6-n-butyl-4-n-propyl- Whilst the first, second, third and fourteenth derivatives listed above are preferred, an especially useful triazolopyrimidine for use in the compositions of the invention is the first derivative, namely 2-amino-6-methyl-5-oxo-4-n-propyl-4,5-dihydro-s-triazolo [1,5-α] pyrimidine having the formula:

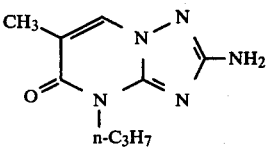

Formula III

This compound is typical of the foregoing s-triazolopyrimidines and has an $LD_{50}$ value of 160 mg/kg (oral, male rats) which is indicative of the highly favourable toxicities which can be expected for the class, bearing in mind the extremely small amounts it is necessary to use in compositions according to the present invention because of their powerful emetic properties.

As used in this specification the term "toxic chemical substance" is intended to refer to chemicals having a utility in industry, agriculture or the home which are toxic to human beings when orally ingested. The term does not include toxic chemicals for which, upon ingestion, the induction of emesis is inadvisable on medical grounds, for example corrosive poisons such as concentrated acids or alkalis.

Preferred compositions according to the invention are compositions comprising a pesticide.

The term "pesticide" refers to biologically-active compositions containing chemicals which are effective in killing or repelling undesirable pests or preventing or controlling their growth. The pests may be plants, insects, mites, rodents, nematodes, microorganisms, algae, fungi, bacteria, viruses and the like. The term "pesticide" may also refer to compositions or chemicals which control or modify the rate of growth, or growth or mode of development, of desirable plant species. All these chemicals and compositions are commonly known as herbicides, fungicides, insecticides, nematocides, miticides, molluscicides, anti-viral agents, algicides, bactericides, plant growth regulants, defoliants, insect attractants and repellents, and the like.

Particularly preferred compositions according to the invention are compositions comprising an insecticide; and, more particularly, compositions comprising organo-phosphorus, carbamate, or oxime carbamate insecticides. Examples of these classes of insecticides for use in the practice of the invention are set out in the Table below.

| COMMON NAME | CHEMICAL NAME |
|---|---|
| Carbaryl | 1-naphthyl methylcarbamate |
| Parathion-Methyl | dimethyl 4-nitrophenyl phosphorothionate |
| Malathion | S-[1,2-di(ethoxycarbonyl)ethyl] dimethyl phosphorothiolothionate |
| Diazinon | diethyl 2-isopropyl-6-methyl-4-pyrimidinyl phosphorothioate |
| Fenitrothion | dimethyl 3-methyl-4-nitrophenyl phosphorothioate |
| Azinphos-Ethyl | diethyl S[(4-oxo-1,2,3-benzotriazin-3(4H)-yl) methyl]phosphorothioiothionate |
| Parathion | diethyl 4-nitrophenyl phosphorothionate |
| Phorate | diethyl S-(ethylthiomethyl) phosphorothiolothionate |
| Carbofuran | 2,3-dihydro-2,2-dimethylbenzofuran-7-yl methylcarbamate |
| Monocrotophos | dimethyl cis-1-methyl-2-methyl carbamoylvinyl phosphate |
| Dimethoate | dimethyl S-methylcarbamoylmethyl phosphorothiolothionate |
| Methomyl | 1-(methylthio)ethylideneamino methylcarbamate |
| Aldicarb | 2-methyl-2-(methylthio)propylideneamino methylcarbamate. |
| Oxamyl | N,N-dimethyl-α-methylcarbamoyloxy-imino-α-(methylthio)acetamide. |
| Dichlorvos | dimethyl 2,2-dichlorovinyl phosphate. |

Further compositions according to the invention comprise pesticides which behave as "uncouplers of oxidative phosphorylation" that is to say pesticides having a biological mode of action which interferes with the production of ATP from ADP in living cells. Nitro-substituted phenols such as 4,6-dinitro-o-cresol, common name DNOC, behave in this manner.

Yet further compositions according to the invention comprise an insecticidal pyrethroid. By the term 'pyrethroid' is meant an insecticidal ester of a suitably substituted cyclopropane carboxylic acid or suitably substituted arylacetic acid and a suitably substituted alcohol or cyanhydrin. Preferably the configuration of the cyclopropane carboxylic acid is 1R, cis- and that of the arylacetic acid, alcohol, and cyanhydrin is S. Particular examples of pyrethroids for use in the practice of the invention are:

S-3-phenoxy-α-cyanobenzyl (1R, cis)-2-(2,2-dibromovinyl)-3,3-dimethylcyclopropane-1-carboxylate, which has the common name 'Decamethrin';

3-Phenoxybenzyl 2-(2,2-dichlorovinyl)-3,3-dimethylcyclopropan-1-carboxylate, having the common name 'Permethrin';

3-Phenoxy-α-cyanobenzyl-2-(2,2-dichlorovinyl)-3,3-dimethylcyclopropan-1-carboxylate, having the common name 'Cypermethrin';

3-Phenoxy-α-cyanobenzyl-4-chlorophenyl-α'-isopropyl phenylacetate, having the common name 'Phenovalerate'; and 3-Phenoxy-α-cyanobenzyl-2,2,3,3,-tetramethylcyclopropane-1-carboxylate.

A molluscicidal composition according to the invention comprises metaldehyde.

Chemical substances other than pesticides to which the invention may be applied may be found in industry and in the home. Examples of such substances are antifreeze mixtures comprising ethylene glycol; brake fluids; petroleum tar distillates such as "Jeyes Fluid" and creosote; carbolic acid preparations; bleaching fluids such as hypochlorites; and industrial solvents such as dry-cleaning solvents and industrial methylated spirit comprising methyl, ethyl, or isopropyl alcohols and preparations, e.g. hair sprays, containing them. The invention may also be applied to drugs, and in particular to drugs such as sleeping pills (e.g. barbiturates) which are popular as a means of attempting suicide. In compositions intended to be taken orally the concentration of emetic must not be so high that a normal does has emetic effects.

The amount of the toxic chemical substance present in the compositions of the invention is generally from 0.1 to 99.9% by weight.

The compositions of the invention may be solids, e.g. granules or pellets, or liquids, e.g. aqueous solutions.

In a preferred aspect the invention provides a concentrated pesticidal composition comprising a liquid pesticidal composition and a triazolo-pyrimidine as hereinbefore defined. Preferably the pesticide is an insecticide.

The amount of pesticide present in the liquid composition is usually from 0.01 to 6.0 pounds per Imperial gallon (1 gram to 600 grams per liter) and preferably from 0.5 to 4.0 pounds per gallon (50 to 400 grams per liter).

Preferably the pesticidal composition also comprises a surface active agent. Surface-active agents may be cationic, non-ionic or anionic. Examples of non-ionic surface-active agents for use in pesticidal compositions of the invention include the condensation products of ethylene oxide with alkyl phenols such as octylphenol, nonylphenol and octylcresol. Other non-ionic agents are the partial esters derived from long chain fatty acids and hexitol anhydrides, for example sorbitan monolaurate; the condensation products of the said partial esters with ethylene oxide; and the lecithins. Examples of cationic surface-active agents include quaternary salts and condensates of ethylene oxide with amines, for example the substances sold under the Trade Marks "Ethomeen", "Ethoduomeen", "Duoquad" and "Arquad".

The emetic properties of the invention compositions are primarily determined by the amount of triazolopyrimidine they contain. In deciding the most appropriate amount of triazolopyramidine (I) to use in any composition, regard must be had to the efficacy of the chosen triazolopyrimidine relative to the toxicity of the chemical substance. The amount of triazolopyrimidine to be included is such that the composition contains sufficient of the triazolopyrimidine (I) to give it emetic properties.

Compositions according to the invention conveniently contain from 0.01 to 5 parts by weight of the triazolopyrimidine (I) per 100 parts of the composition. To obtain the necessary balance between toxic and emetic properties the proportion of toxic chemical may, if appropriate, be reduced, and the proportion of inert diluent or carrier increased.

In a further aspect the invention provides a method of avoiding or reducing the toxifying effect of chemicals ingested by a mammal and especially a human, which comprises administering to the affected mammal or human an emetically effective amount of an s-triazolo-[1,5-a] pyrimidine derivative as defined above.

The invention is illustrated by the following Examples, No. 1 to 14 of which are pesticide formulations of varying kinds; No. 14 to 26 illustrate other toxic chemical compositions; and Examples 27 and 28 illustrate, respectively, the efficacy of safeguarded compositions according to the invention, and the delay in gastric emptying caused by the emetic. In the Examples proportions of constituents of compositions are in grams unless otherwise stated.

EXAMPLE 1

This Example illustrates a composition according to the invention which comprises 2-amino-6-methyl-5-oxo-4-n-propyl-4,5-dihydro-5-triazolo [1,5-α] pyrimidine, (hereinafter referred to as "Emetic of Formula III") and Malathion.

|  | % w/v |
| --- | --- |
| Malathion | 90 |
| Emetic of formula III above | 0.05 |
| Aromasol H (a solvent mixture of alkyl benzenes) | to 100 ml |

EXAMPLE 2

This Example illustrates a composition according to the invention which is an emulsifiable concentrate comprising parathion.

|  | % w/v |
| --- | --- |
| Parathion | 50 |
| Emetic of formula III | 0.05 |
| Arylan CA (calcium dodecyl benzene sulphonate) | 5 |
| Lubrol N13 (a condensate of 1 mole of nonyl phenol with 13 moles of ethylene oxide) | 5 |
| Xylene | to 100 ml |

EXAMPLE 3

This Example illustrates a wettable powder containing 25% on a weight/weight basis, of the insecticide malathion. The constituents, and proportions, are as follows:

|  | % w/w |
| --- | --- |
| Malathion | 25 |
| Emetic of formula III | 0.03 |
| Kaolin clay | 28.5 |
| Polyfon H (a polymeric sodium lignin sulphonate) | 3.0 |
| Pluronic F68 (a polypropylene polyethylene block copolymer) | 2.0 |
| China clay | to 100 grams |

The constituents are mixed together and then ground.

A similar formulation was prepared using instead of the emetic of formula III twice the amount of the emetic of formula:

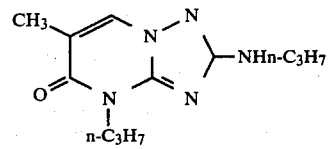

EXAMPLE 4

This Example illustrates a composition according to the invention which comprises a herbicide.

|  | % w/v |
| --- | --- |
| Emetic of formula III | 0.05 |
| Potassium 2,4-dichlorophenoxy acetate | 40 |
| Water | to 100 ml |

EXAMPLE 5

This Example illustrates a miscible liquid formulation containing the insecticide dimethoate.

|  | % w/v |
| --- | --- |
| Dimethoate | 40 |
| Lubrol N13 | 1 |
| Emetic of formula III | 0.05 |
| Ethyl cellusolve | to 100 ml |

EXAMPLE 6

This Example illustrates a wettable powder formulation containing an insecticide. The constituents were mixed and ground.

|  | % w/w |
| --- | --- |
| Azinphos ethyl | 25 |
| Emetic of formula III | 0.5 |
| Dispersol % (a mixture of sodium sulphate and a condensate of formaldehyde with the sodium salt of naphthalene sulphonic acid) | 5 |
| Vancell E (lignin sulphonate - as sodium salt) | 5 |
| Silica K320 | 10 |
| China clay | to 100 grams |

In a further, similar, formulation the emetic of formula III was replaced by twice the amount of the emetics having the following formulae:

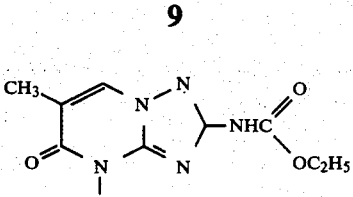

and

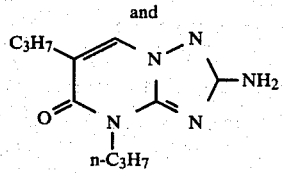

EXAMPLE 7

This Example illustrates an emulsifiable concentrate containing 20% (on a weight/volume basis) of diazinon.

|  | % w/v |
|---|---|
| Diazinon | 20 |
| Emetic of formula III | 0.05 |
| Arylan CA (calcium dodecyl benzene sulphonate) | 5 |
| Lubrol N13 (a condensate or 13 moles of nonyl phenol with 13 moles of ethylene oxide) | 5 |
| Epichlorhydrin | 3 |
| Aromasol H | to 100 ml |

In exactly the same manner, using the same proportions of constituents, similar preparations were made replacing the diazinon with (a) 50 g of dichlorvos and (b) 175 g of phorate.

EXAMPLE 8

This Example illustrates a flowable liquid concentrate containing 50% of the insecticide carbaryl. The proportions (on a weight/volume basis) of the various constituents are as follows:

|  | % w/v |
|---|---|
| Carbaryl | 50 |
| Emetic of formula III | 0.03 |
| Polyfon H (a polymeric sodium lignin sulphonate dispersing agent) | 5 |
| Bentonite (sodium montmorillonite) | 1 |
| Water | to 100 ml |

The carbaryl was finely ground and dispersed in about 90% of the water containing the emetic and Polyfon H. The bentonite was separately dispersed in about 10% of the water and then incorporated into the previously prepared mixture.

EXAMPLE 9

This Example illustrates a granular pesticide formulation.

|  | % w/w |
|---|---|
| Aldicarb | 5 |
| Emetic of formula III | 0.05 |
| Gypsum 10/40 B.S. mesh granules | to 100 grams |

The aldicarb is dissolved in a solvent and then sprayed onto the gypsum in a fluid bed granulator.

EXAMPLE 10

This Example illustrates a water-soluble powder formulation of the pesticide methomyl.

|  | % w/w |
|---|---|
| Methomyl | 60 |
| Emetic of formula III | 0.05 |
| Aerosol OT/B (dioctyl sodium sulphosuccinate adsorbed onto urea) | 5 |
| Sodium acetate | to 100 grams |

The constituents were mixed and ground together.

EXAMPLE 11

This Example illustrates a soluble-liquid formulation of a pesticide.

|  | % w/v |
|---|---|
| Oxamyl | 20 |
| Emetic of formula III | 0.03 |
| Ethylene glycol | 10 |
| Water | to 100 ml |

EXAMPLE 12

This Example illustrates an emulsifiable concentrate containing fenitrothion.

|  |  | % w/v |
|---|---|---|
| Fenitrothion |  | 50 |
| Emetic of formula III |  | 0.05 |
| Monolan M (an ethylene oxide/propylene oxide copolymer) |  | 4.5 |
| Ethylan A.C. | (a blend of anionic and non-ionic surface active agents supplied by Lankro Chemicals Ltd) | 3.0 |
| Arylan B.A. | | 7.5 |
| Epichlorhydrin |  | 3.0 |
| Aromasol H |  | to 100 ml |

EXAMPLE 13

This Example illustrates an extruded rodenticide bait pellet.

|  | % w/v |
|---|---|
| Sodium chloride | 0.5 |
| Monosodium glutamate | 0.5 |
| China clay | 5.0 |
| Pigments | 0.2 |
| Whole ground wheat | to 100 grams |

The above mix is extruded into granules.

The granules are then sprayed with a concentrate containing:

| | % w/v |
|---|---|
| Rodenticide (difenacoum or brodifacoum) | 0.25 |
| Emetic of formula III | 0.05 |
| Triethanolamine | 3 |
| 4-Nitrophenol | 2.5 |
| Polyethylene glycol (Molecular weight 200) | 3 |
| Propylene glycol | to 100 ml | to a level of 2% w/w on the granules. Alternatively the formulations above are mixed as one and extruded to obtain pellets.

Difenacoum is: 3-(3-biphenyl-4-yl-1,2,3,4-tetrahydro-1-naphthyl)-4-hydroxycoumarin.

Brodifacoum is: 3-[3-(4'-bromobiphenyl-4-yl)-1,2,3,4-tetrahydro-1-naphthyl]-4-hydroxycoumarin.

EXAMPLE 14

This Example illustrates a rodenticide preparation in the form of a contact powder which rodents pick up upon their fur and ingest whilst preening themselves.

| | % w/w |
|---|---|
| Emetic of formula III | 0.05 |
| Difenacoum rodenticide | 0.2 |
| Talc | to 100 grams |

Instead of talc the following were used (singly or in admixture); basic slag, china clay and kieselguhr in further formulations, the difenacoum being replaced by the rodenticide brodifacoum. Both these latter rodenticide names are common names.

EXAMPLE 15

This Example illustrates a composition according to the invention which comprises a pharmaceutical chemical.

| | % w/v |
|---|---|
| Phenobarbitone | 50 mg |
| Dextrose | 50 mg |
| Emetic of formula III | 0.2 mg |

The composition was produced by admixture of the ingredients and then formulated in the form of a tablet.

EXAMPLE 16

This Example illustrates a composition according to the invention which comprises a pharmaceutical chemical.

| | % w/v |
|---|---|
| Aspirin (acetylsalicylic acid) | 100 mg |
| Emetic of formula III | 0.1 mg |

The composition was produced by admixture of the ingredients and then formulated in the form of a tablet.

EXAMPLE 17

This Example illustrates a composition according to the invention which comprises an anti-freeze mixture.

| | % w/v |
|---|---|
| Emetic of formula III | 0.05 |
| Sodium Tetraborate 10 $H_2O$ | 3 |
| Phosphoric acid | 1 |
| Triethanolamine | 2 |
| Benzotriazole | 0.2 |
| Ethylene glycol | to 100 ml |

EXAMPLE 18

This Example illustrates a composition according to the invention comprising an anti-freeze mixture.

| | % w/v |
|---|---|
| Emetic of formula III | 0.05 |
| Borax | 3.0 |
| Phosphoric acid | 0.95 |
| Triethanolamine | 2.1 |
| Benzotriazole | 0.2 |
| Water | 4 |
| Diethylene glycol | to 100 ml |

EXAMPLE 19

This Example illustrates an industrial "methylated spirits" formulation (a) and "methylated spirit" for home use (B).

| | | % w/v |
|---|---|---|
| A. | Methyl alcohol | 4.9 |
| | Emetic of formula III | 0.05 |
| | Pyridine base | 0.5 |
| | Ethyl alcohol | to 100 ml |
| B. | Methyl alcohol | 95 |
| | Emetic of formula III | 0.05 |
| | Mineral naphtha | 0.4 |
| | Pyridine bases | 0.5 |
| | Methyl violet | 0.0002 |
| | Ethyl alcohol | to 100 ml |

EXAMPLE 20

This Example illustrates a washing-up liquid.

| | % w/v |
|---|---|
| Sodium linear alkyl benzene sulphonate | 15 |
| Sodium linear alcohol ($C_{12-15}$) ether sulphate containing 3 moles of ethylene oxide | 5 |
| Coco fatty acid diethanolamide | 1 |
| Perfume | 0.1 |
| Dye | 0.01 |
| Ethyl alcohol | 5 |
| Sodium chloride | 6 |
| Emetic of formula III | 0.02 |
| Water | to 100 ml |

EXAMPLE 21

This Example illustrates a liquid metal polish preparation.

| | % w/w |
|---|---|
| Emetic of formula III | 0.05 |
| Diglycol stearate | 5 |
| Water | 20 |

-continued

|  | % w/w |
| --- | --- |
| Oleic acid | 4 |
| Mineral oil | 5 |
| Industrial methyl alcohol (IMS) ("methylated spirits") | 10 |
| Ammonia (0.910) | 3 |
| Ground chalk | 25 |
| Water | to 100 grams |

The diglycol stearate and emetic are dissolved in the water and to this solution are added an emulsion of a mixture of the oleic acid, mineral oil and IMS to which the ammonia is added. The ground chalk is worked-in with vigorous stirring and then, in small amounts at a time, the remainder of the water, continuing vigorous stirring.

EXAMPLE 22

This Example illustrates a pine oil disinfectant.

|  | % w/v |
| --- | --- |
| Emetic of formula III | 0.05 |
| Pine oil | 80 |
| Sulphated castor oil | 19.05 |

EXAMPLE 23

This Example illustrates a cresol disinfectant preparation for industrial or domestic use.

|  | % w/w |
| --- | --- |
| Rosin | 24 |
| Caustic soda | 7 |
| Creosote oil | 24 |
| Carbolic acid | 0.4 |
| Emetic of formula III | 0.05 |
| Water | to 100 grams |

EXAMPLE 24

The following Example illustrates an after-shave formulation containing a safe-guarding proportion of the emetic of formula III.

|  | % w/w |
| --- | --- |
| Glycerin | 5 |
| Alum | 1 |
| Zinc sulphophenolate | 0.5 |
| Propyl alcohol | 10 |
| Rose water | 10 |
| Perfume | 0.5 |
| Emetic of formula III | 0.05 |
| Ethyl alcohol (96%) | to 100 grams |

EXAMPLE 25

The following Example illustrates an Eau de Cologne formulation containing the emetic of formula III above.

|  | % w/v |
| --- | --- |
| Emetic of formula III | 0.05 |
| Lemon oil | 0.9 |
| Bergamot oil | 0.8 |
| Orange oil, sweet | 0.25 |
| Lavender oil | 0.20 |
| Mandarin oil | 0.16 |
| Petitgram oil, Grasse | 0.16 |
| Benzoin resinoid | 0.14 |
| Neroti oil, original | 0.14 |
| Orange oil, bitter | 0.14 |
| Lime oil | 0.14 |
| Rosemary oil | 0.05 |
| Eugenol | 0.03 |
| Cumene aldehyde | 0.025 |
| Muscated sage oil | 0.015 |
| Hyssop oil | 0.005 |
| Cardamon oil | 0.005 |
| Iris concentrate | 0.005 |
| Alcohol (96%) | 86.9 |
| Distilled water | to 100 |

EXAMPLE 26

This Example illustrates a liquid preparation useful for removing varnish from finger nails.

|  | % w/w |
| --- | --- |
| Amyl acetate | 20 |
| Ethyl acetate | 20 |
| Emetic of formula III | 0.01 |
| Acetone | to 100 grams |

The emetic was dissolved into the organic solvents. Perfume was added to complete the cosmetic preparation.

EXAMPLE 27

This Example demonstrates the efficacy of safe-guarded compositions according to the invention.

Parathion and malathion alone, and invention compositions comprising parathion or malathion and the compound 2-amino-6-methyl-5-oxo-4-n-propyl-4,5-dihydro-s-triazolo [1,5-α] pyrimidine having the formula:

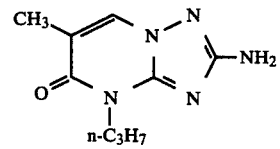

were orally administered to 2 animals [Macaca fascicularis (Cynomolgus monkeys)] and the time lapse for emesis to take place recorded. The results of the experiment are shown in Table 1 below:

TABLE 1

| DOSAGE SUBSTANCE | RATE OF DOSAGE IN MILLIGRAMS PER KILOGRAM OF LIVE BODY WEIGHT | ANIMALS IN WHICH EMESIS TOOK PLACE | TIME TO EMESIS IN HOURS AND MINUTES | SURVIVAL NUMBER AFTER 14 DAYS |
| --- | --- | --- | --- | --- |
| Parathion only | 200 | 1 | 1 hour | 0 |
| Malathion only | 500 | 1 | 1 hour 35 minutes | 0 |
| Parathion | 200 | 2 | 6 minutes | 2 |

TABLE 1-continued

| DOSAGE SUBSTANCE | RATE OF DOSAGE IN MILLIGRAMS PER KILOGRAM OF LIVE BODY WEIGHT | ANIMALS IN WHICH EMESIS TOOK PLACE | TIME TO EMESIS IN HOURS AND MINUTES | SURVIVAL NUMBER AFTER 14 DAYS |
|---|---|---|---|---|
| Emetic of Formula III (admixture) | 2 | | and 10 minutes respectively | |
| Malathion | 2000 | 2 | 2 minutes | 2 |
| Emetic of Formula III (admixture) | 2 | | and 10 minutes respectively | |

The results demonstrate clearly the safeguarded properties of compositions according to the invention. The $LD_{50}$ values for Parathion only, and Malathion only, are, respectively, approximately 100, and between 270 to 400, milligrams per kilogram of live body weight; the corresponding $LD_{50}$ values for the compositions are approximately 400 and greater than 2000.

EXAMPLE 28

This Example illustrates the delay in gastric emptying in animals dosed with sub-emetic amounts of the emetic of formula III.

Rats, mice and Cynomolgus monkeys (Macaca fascicularis) were orally and subcutaneously (rats and mice only) dosed with compositions containing the compound 2-amino-6-methyl-5-oxo-4-n-propyl-4,5-dihydro-s-triazolo pyrimidine having the formula:

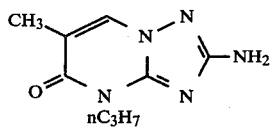

The dosage rate for the monkeys was approximately one-tenth of that required to produce emesis.

The results are given in Table 2 below and show the percentage inhibition of gastric emptying 1 hour after dosing against control experiments in which the foregoing substance was omitted from the composition administered. All compositions contained either radio-labelled chromium (sodium chromate) (rats and mice) or phenol-red dye (monkeys) and the stomach contents of the animals were analysed to determine the amount present one hour after dosing.

TABLE 2

| SPECIES | DOSAGE RATE IN MILLIGRAMS PER KILOGRAM OF LIVE BODY WEIGHT | ADMINISTRATION | PERCENTAGE INHIBITION OF GASTRIC EMPTYING |
|---|---|---|---|
| Mice | 1.0 | Subcutaneous | 86 |
| | 2.5 | oral | 91 |
| Rats | 0.1 | oral | 37 |
| | 1.0 | oral | 68 |
| | 0.1 | Subcutaneous | 48 |
| | 1.0 | Subcutaneous | 75 |
| Monkeys | 0.2 | oral | 61 |

These remarkable and surprising results clearly demonstrate that an emetic constituent of compositions according to the invention, even at sub-emetic dosage rates, achieves, after oral ingestion, a substantial reduction in the uptake by their bodies of their stomach contents by animals, thereby lessening the onset of toxic effects and enhancing their prospects of survival, more especially by providing more time for emesis to take place (in those instances where an emetic amount is administered) and/or other remedial measures to be taken, after oral ingestion.

In the foregoing text and Examples the following:
"AROMASOL" H
"DISPERSOL" T
"LUBROL" N13
"AEROSOL" OT/B
"ETHYLAN" AC
"ARYLAN" CA
"ARYLAN" 13A
"POLYFON" H
"PLURONIC" F68
"VANCELL" E
"CRYPOUM"
"MONOLAN" M
are Trade Marks or Trade Names.

We claim:

1. An emetic composition comprising a toxic amount of a toxic chemical substance which is other than a herbicidal bipyridylium quaternary salt, which is not intended for oral ingestion but when so orally ingested passes into the blood through the stomach and digestive tract and for which treatment by induction of emesis is medically advisable and an emetically effective amount of 0.01 to 5 parts by weight per 100 parts of the composition of an emetically active s-triazolo [1,5-a] pyrimidine derivative of the formula

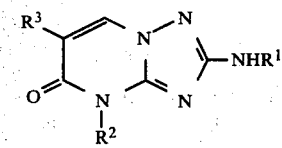

wherein $R^1$ is hydrogen, a $C_{1-4}$ alkyl radical, or a $COOC_2H_5$ radical; $R^2$ is a $C_{1-4}$ alkyl radical or an allyl radical, and $R^3$ is a $C_{1-4}$ alkyl radical, or a pharmaceutically acceptable emetically active addition salt thereof, the ratio of emetic to toxic chemical being such as to induce emesis when the composition is orally ingested.

2. A composition according to claim 1 wherein the emetically active s-triazolo-[1,5-α]pyrimidine is selected from the group consisting of:

6-methyl-4-n-propyl-2-n-propylamino-5-oxo-4,5-dihydro-s-triazolo[1,5-a]pyrimidine, 2-amino-6-methyl-4-allyl-5-oxo-4,5-dihydro-s-triazolo triazolo triazolo[1,5a]pyrimidine, 2-amino-4,6-di-n-propyl-5-oxo-4,5-dihydro-s-triazolo[1,5-a]pyrimidine, and 2-ethoxycarbonylamino-6-methyl-4-n-propyl-5-oxo-4,5-dihydro-s-triazolo[1,5-α]pyrimidine.

3. An emetic liquid organophosphorus insecticide composition comprising, in a liquid, 1 gram to 600 grams per liter of a toxic organophosphorus insecticide and from 0.01 to 5 parts, per 100 parts by weight of the composition, of an emetically active s-triazolo-[1,5-α]pyrimidine derivative of the formula:

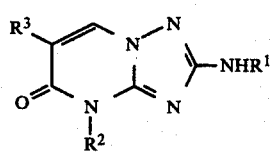

wherein $R^1$ is hydrogen, a $C_{1-4}$ alkyl radical, or a COOEt radical; $R^2$ is a $C_{1-4}$ alkyl radical or an allyl radical, and $R^3$ is a $C_{1-4}$ alkyl radical, or a pharmaceutically acceptable emetically active addition salt thereof.

4. An emetic composition according to claim 1 wherein the emetic is 2-amino-6-methyl-5-oxo-4-n-propyl-4,5-dihydro-s-triazolo[1,5-α]pyrimidine having the formula:

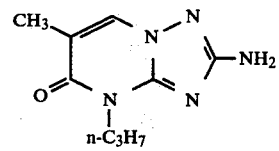

5. An emetic composition according to claim 1 wherein the toxic chemical substance is a pesticide.

6. An emetic composition according to claim 1 wherein the toxic chemical is an insecticide.

7. An emetic composition as claimed in claim 1 and containing a surface active agent.

8. A method of avoiding or reducing the toxifying effect of a toxic chemical which is other than a herbicidal bipyridylium quaternary salt and which is not intended for oral ingestion but when so ingested passes into the blood through the stomach and digestive tract and for which treatment by induction of emesis is medically advisable ingested by a mammal which comprises administering to said mammal an emetically effective amount of an s-triazolo-[1,5-α]pyrimidine derivative of the formula

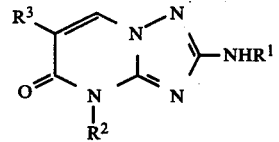

wherein $R^1$ is hydrogen, a $C_{1-4}$ alkyl radical, or a COOEt radical; $R^2$ is a $C_{1-4}$ alkyl radical or an allyl radical; and $R^3$ is a $C_{1-4}$ alkyl radical, or a pharmaceutically acceptable emetically active addition salt thereof.

* * * * *